(12) United States Patent
Miao et al.

(10) Patent No.: US 10,436,932 B2
(45) Date of Patent: Oct. 8, 2019

(54) INSPECTION SYSTEMS FOR QUARANTINE AND METHODS THEREOF

(71) Applicants: NUCTECH COMPANY LIMITED, Beijing (CN); CINTS CO. LTD., Beijing (CN)

(72) Inventors: Qitian Miao, Beijing (CN); Zhiqiang Chen, Beijing (CN); Li Zhang, Beijing (CN); Yunda Sun, Beijing (CN); Ming Huang, Beijing (CN); Qingping Huang, Beijing (CN); Ming Hu, Beijing (CN); Lei Lei, Beijing (CN); Jie Xia, Beijing (CN)

(73) Assignees: NUCTECH COMPANY LIMITED, Beijing (CN); CINTS CO., LTD., Beijing (CN)

( * ) Notice: Subject to any disclaimer, the term of this patent is extended or adjusted under 35 U.S.C. 154(b) by 192 days.

(21) Appl. No.: 15/279,207

(22) Filed: Sep. 28, 2016

(65) Prior Publication Data

US 2017/0184756 A1 Jun. 29, 2017

(30) Foreign Application Priority Data

Dec. 29, 2015 (CN) .......................... 2015 1 1010081

(51) Int. Cl.
*G01N 23/046* (2018.01)
*G01V 5/00* (2006.01)

(52) U.S. Cl.
CPC ............ *G01V 5/005* (2013.01); *G01V 5/0041* (2013.01)

(58) Field of Classification Search
CPC ..... G01V 5/005; G01V 5/0041; G01N 23/046

USPC .......................................... 378/57
See application file for complete search history.

(56) References Cited

U.S. PATENT DOCUMENTS

| 4,539,648 | A | 9/1985 | Schatzki |
| 5,367,552 | A | 11/1994 | Peschmann |
| 8,036,337 | B2 | 10/2011 | Zhang et al. |
| 8,320,523 | B2 | 11/2012 | Zhang et al. |
| 9,412,019 | B2 | 8/2016 | Chen et al. |

(Continued)

FOREIGN PATENT DOCUMENTS

| CN | 101403710 A | 4/2009 |
| CN | 101435783 A | 5/2009 |

(Continued)

OTHER PUBLICATIONS

Extended European Search Report as issued in European Patent Application No. 16191227.4, dated May 17, 2017.

(Continued)

*Primary Examiner* — Courtney D Thomas
(74) *Attorney, Agent, or Firm* — Pillsbury Winthrop Shaw Pittman LLP (57) ABSTRACT

The present disclosure discloses an inspection system for quarantine and a method thereof. The CT technology is applied to the field of quarantine supervision, overcoming a problem of objects in an image of a single-view or a multi-view X-ray machine being overlapped, as well as a problem of organics including contrabands in a conventional CT image being not highlighted, not elaborated, and having bad contrast. Accuracy and efficiency of inspecting an object by human operator for quarantine inspection can be considerably improved, which is of a high application value.

24 Claims, 4 Drawing Sheets

(56) References Cited

U.S. PATENT DOCUMENTS

| | | | |
|---|---|---|---|
| 9,465,975 B2 | 10/2016 | Li et al. | |
| 9,495,772 B2 | 11/2016 | Shen et al. | |
| 10,102,641 B2 | 10/2018 | Chen et al. | |
| 2005/0276376 A1 | 12/2005 | Eilbert | |
| 2009/0010386 A1* | 1/2009 | Peschmann | G01N 23/223 378/57 |
| 2009/0129544 A1* | 5/2009 | Chen | G01N 23/04 378/62 |
| 2010/0284514 A1 | 11/2010 | Zhang | |

FOREIGN PATENT DOCUMENTS

| | | |
|---|---|---|
| CN | 101470082 A | 7/2009 |
| CN | 101641589 A | 2/2010 |
| CN | 102162798 A | 8/2011 |
| CN | 102435620 A | 5/2012 |
| CN | 102565107 A | 7/2012 |
| CN | 102590234 A | 7/2012 |
| CN | 103900503 A | 7/2014 |
| CN | 103903297 A | 7/2014 |
| CN | 103913472 A | 7/2014 |
| CN | 103926628 A | 7/2014 |
| CN | 204008508 U | 12/2014 |
| CN | 105004741 A | 10/2015 |
| CN | 205353380 U | 6/2016 |
| EP | 0 223 545 A2 | 5/1987 |
| EP | 2 309 257 A1 | 4/2011 |
| KR | 10-2015-0117417 A | 10/2015 |
| WO | WO 2013/078344 A1 | 5/2013 |

OTHER PUBLICATIONS

International Search Report and the Written Opinion of the International Searching Authority as issued in International Patent Application No. PCT/CN2016/097577, dated Nov. 24, 2016.

Examination Report as issued in Australian Patent Application No. 2016235025 dated Aug. 28, 2017.

Office Action as issued in Chinese Patent Application No. 201511009740.2, dated May 4, 2017.

Office Action as issued in Canadian Patent Application No. 2,943,764, dated Jul. 26, 2018.

Taina, I. A., et al., "Application of X-ray computed tomography to soil science: A literature review," *Canadian Journal of Soil Science, Department of Land Resource Science, University of Guelph*, <http://www.nrcresearchpress.com/doi/10.4141/CJSS06027#.W1XTGdVKhEZ>, Oct. 2, 2007, 25 pages.

Office Action as issued in U.S. Appl. No. 15/279,239, dated Aug. 27, 2018.

Notice of Allowance as issued in U.S. Appl. No. 15/279,239, dated Dec. 19, 2018.

Office Action as issued in Chinese Patent Application No. 201511010081.4, dated Dec. 29, 2018.

Notice of Allowance as issued in U.S. Appl. No. 15/279,239, dated May 9, 2019.

* cited by examiner

INSPECTION SYSTEMS FOR QUARANTINE AND METHODS THEREOF

TECHNICAL FIELD

The present disclosure relates to the field of radiation imaging inspection technology, and in particular, to inspection systems for quarantine and methods thereof.

BACKGROUND

Compared to a single view X-ray machine or a multi-view X-ray machine, CT (Computed Tomography) technology plays an important role on various applications such as security, since CT technology can eliminate an effect of object overlap to a great extent. However, in the case of security, contraband (on which a human operator focuses) can be of various types, including not only guns and cutters made of metal, but also sharp products made of glass, ceramic and/or aluminum which are referred to as mixtures, as well as various exploding devices which are categorized as organic, containing a flammable and/or explosive liquid. Since there are so many categories of objects required to be imaged, any of the categories cannot get a most notable and most elaborate display effect, which affects user experience and affects the inspection ability of the human operator using a CT system to some extent.

SUMMARY

The contraband on which a human operator that exercises quarantine supervision functions, focuses most is various types of plants and animals, including various types of fruits, vegetables, seeds, insects, meat products, etc. This contraband in inspection and quarantine may be divided into many sub-categories, which basically belong to organic. Currently, a human operator in the field urgently desires that a single-view or a multi-view X-ray machine may be replaced with a more advanced CT system. However, an imaging quality of contraband in inspection and quarantine cannot be improved due to lack of a quarantine-dedicated CT system, which causes great difficulties in identifying a target object rapidly and accurately by the human operator in the field. There is no quarantine-dedicated CT inspection system and method thereof found in documents and patents of the prior art.

Taking one or more problems in the prior art into consideration, the present disclosure provides inspection systems for quarantine and methods thereof.

In an aspect of the present disclosure, an inspection system for quarantine is provided. The inspection system for quarantine includes: a CT scan device configured to perform CT scan on an object to obtain projection data; a computing unit coupled to the CT scan device, configured to perform a reconstruction, based on the projection data, to obtain image data reflecting internal features of the object being scanned, and determine an organic part and/or contraband part of the object being scanned; and a display unit coupled to the computing unit, configured to enhance or highlight display of the determined organic or contraband part relative to other another part.

In some embodiments, the organic part and a non-organic part of the object being scanned are distinguished based on physical attributes of the object being scanned.

In some embodiments, the physical attributes includes at least one selected from: attenuation coefficient, basis-material coefficient, CT number, density and/or effective atomic number.

In some embodiments, contraband and non-contraband are distinguished based on at least one selected from: a physical attribute, a shape feature and/or a texture feature, of the object being scanned.

In some embodiments, the physical attribute comprise at least one selected from: attenuation coefficient, basis-material coefficient, CT number, density and/or effective atomic number.

In some embodiments, the CT scan device performs a single-energy CT scan or a dual-energy CT scan on the object being scanned; reconstructs, by the computing unit, an attenuation-coefficient image, a CT-number image or an effective-atomic-number image, of the object being scanned; and determines the organic and/or contraband part in the object being scanned according to at least one selected from: the shape feature, the texture feature and/or the physical attribute.

In some embodiments, the display unit enhances contrast of the organic and/or contraband part in the object being scanned.

In some embodiments, the display unit stretches the gray-scale of pixels which are classified into the organic and/or contraband part to a larger range.

In some embodiments, the computing unit divides the organic and/or contraband part into a plurality of sub-categories based on a classification standard which is created in advance, and assigns different colors to pixels of the sub-categories.

In some embodiments, the display unit indicates the organic and/or contraband part in the object being scanned.

In some embodiments, the display unit displays the organic and/or contraband part in the object being scanned with a box, an arrow, a flash or an assigned special color.

In some embodiments, the display unit hides a non-organic part and/or non-contraband part in the object being scanned.

In some embodiments, the display unit weakens display of the non-organic and/or non-contraband part in the object being scanned.

In some embodiments, the display unit performs gray-scale range reduction, same color display, gray display, transparency increase or saturation degree decrease on the non-organic and/or non-contraband part in the object being scanned.

In some embodiments, the display unit weakens display of the non-organic and/or non-contraband part, while it enhances display of the organic and/or contraband part.

In some embodiments, the computing unit determines a foreground part of the image data; and removes pixels in the foreground part whose attenuation coefficient, CT number and/or effective atomic number is larger than a predetermined value, so as to eliminate a shield of the foreground part on the organic and/or contraband part.

In some embodiments, the computing unit weakens pixels of the image data whose attenuation coefficient, CT number and/or effective atomic number is larger than a predetermined value.

In some embodiments, the computing unit identifies the contraband part according to a template; and highlights an image of the contraband part by the display unit.

In some embodiments, the inspection system further includes: a DR (Digital-Radiography) scan device configured to operate in synchronization with the CT scan device to obtain a transmitted image, and display a CT image and the transmitted image on a screen of the display unit.

In some embodiments, the computing unit automatically segments an image of the object being scanned which comprises a mixture of multiple kinds of articles into separate articles according to their outline edges, facilitating a human operator to judge the image.

In some embodiments, the computing unit compares an appearance of a 3D image of the object being scanned with a template in a suspect image database; and highlights a suspect object in connection with results of a substance identification.

In some embodiments, the computing unit automatically identifies shape features of a contraband part which are frequently labeled by a user and records the shape features in a database.

In another aspect of the present disclosure, an inspection method for quarantine is provided, including: performing CT scan on an object being scanned to obtain projection data; performing a reconstruction, based on the projection data, to obtain image data reflecting internal features of the object being scanned; determining an organic part and/or a contraband part, of the object being scanned; and enhancing or highlighting display of the determined organic and/or contraband part relative to another part.

With the technical solutions as described above, accuracy and efficiency of inspecting an object by a human operator for quarantine can be improved, which is of a high application value.

DETAILED DESCRIPTION

Hereinafter, preferred embodiments of the present disclosure will be described in detail with reference to the drawings. Although shown in different drawings, the same reference numbers represent the same or similar components. For clarity and conciseness, descriptions on well-known functions and structures will be omitted here to avoid obscuring the subject matter of the present disclosure. Embodiments below are used for explaining the present disclosure, but do not limit the scope of the present disclosure.

Figure 1:
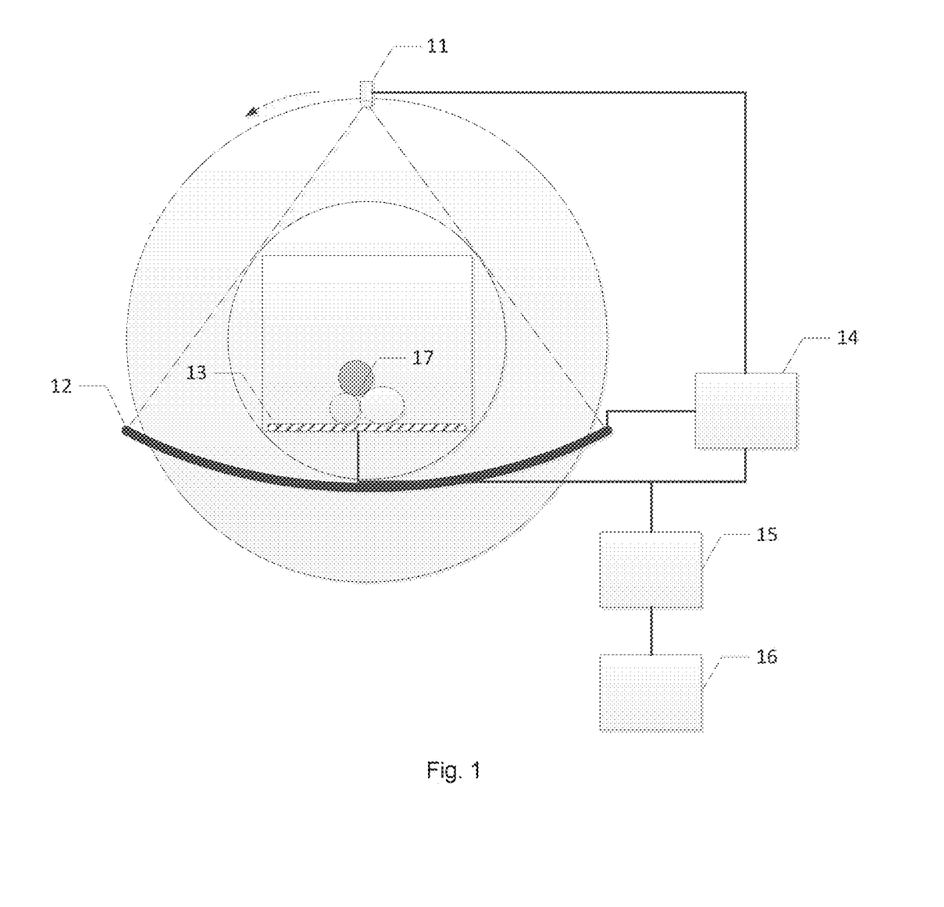
FIG. 1 shows a schematic view of an inspection system according to an embodiment of the present disclosure.

FIG. 1 shows a schematic view of an inspection system according to an embodiment of the present disclosure. As shown in FIG. 1, the inspection system according to the present embodiment includes a CT device for quarantine. The system includes an X-ray source 11, a detection and collection apparatus 12, a conveying apparatus 13, a controller 14, a computing unit 15 such as CPU or GPU, and a display unit 16. The X-ray source 11 and the detection and collection apparatus 12 are installed on a rotation apparatus such as a gantry, and are rotated in a high speed controlled by the controller 14. The controller 14 controls the conveying apparatus 13 such as a belt to convey one or more objects 17 being scanned from one side of the rotation apparatus to the other side at a constant speed. X-rays emitted from the X-ray source 11 are received by a detector of the detection and collection apparatus 12 after they are transmitted through the object being scanned, and are converted by an analog-to-digital A/D conversion circuit to form a digital signal as projection data. The computing unit 15, e.g., an image processing unit, reconstructs the digital signal to be a 3D image which reflects the internal structure and/or material features of the object 17 being scanned, and enhances display of an organic part and/or a contraband part, in of the 3D image, by highlighting the part(s).

In some embodiments, the X-ray source 11 may be a dual-energy X-ray source, and the detector may also receive X-rays with different energies, so that a dual-energy X-ray inspection may be performed on the object 17 being scanned. The CT scan performed here may be a circular scan or the like.

The detection and collection apparatus 12 may be e.g. detectors and data collectors in an integrated module structure, e.g., a flat-panel detector, which may be used for detecting the rays passing through the object being scanned so as to obtain an analog signal, and for converting the analog signal to a digital signal, thereby outputting projection data of the object 17 being scanned for the X-rays.

The controller 14 is connected to the X-ray source 11, the detection and collection apparatus 12 and the conveying apparatus 13, and controls each part of the whole system to work synchronously. The computing unit 15 processes and reconstructs data collected by the data collector, and outputs the result. For example, after the one or more objects 17 are scanned by the dual-energy CT device, the obtained dual-energy 3D image data are input to the computing unit 15; an installed substance identification system is used for performing substance identification on the object being scanned according to the image data, so as to obtain information of different substances, such as effective atomic numbers, densities, etc., and for tinting the 3D image so as to be displayed on a screen of the display unit 16. Also, the article which is judged as the object focused in quarantine (plant, animal, meat, etc.) may be further automatically labeled.

As shown in FIG. 1, the X-ray source 11 is arranged at one side of the object 17 being scanned; and the detection and collection apparatus 12, including the detector and the data collector, is arranged at another side of the object 17 being scanned and is used for obtaining transmission data and/or multi-angle projection data of the object 17 being scanned. A data amplifying circuit is included in the data collector, which may work in a (current) integrated manner or a pulse (counting) manner. A data output cable of the detection and collection apparatus 12 is connected to the controller 14 and the computing unit 15, and the collected data are stored in the storage according to a trigger command. As will be understood by the skilled in the art, the X-ray source and the detector may utilize a structure without a gantry, i.e., a statically distributed multi-light source, in other embodiments.

In addition, the system according to the above embodiment may also integrate a conventional single-view or multi-view X-ray machine for displaying a 3D image and a single-view or multi-view 2D image synchronously and associating them with each other, which facilitates a human operator for quarantine to merge image reading experiences on the 2D image with a great amount of new information contained in the 3D image, so as to upgrade to a new generation inspection technology stably.

Figure 2:
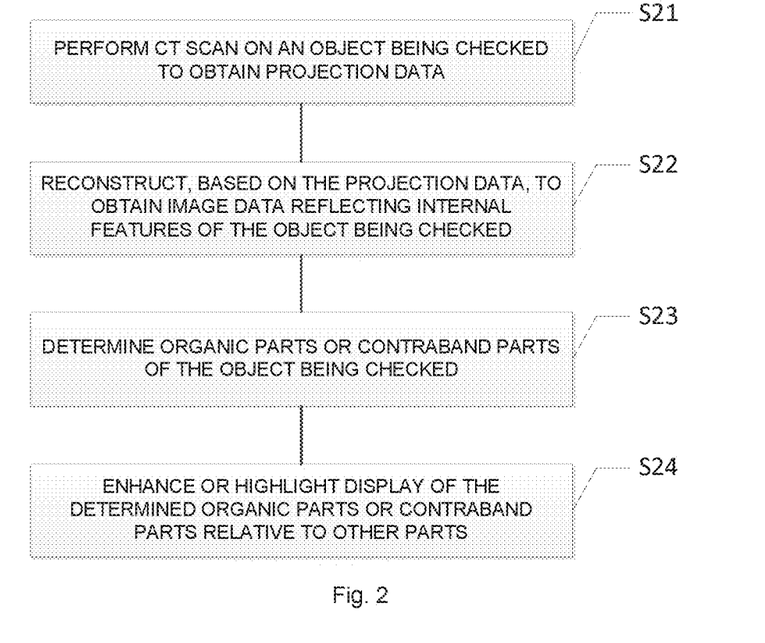
FIG. 2 shows an illustrative flowchart of an inspection method according to an embodiment of the present disclosure.

FIG. 2 shows an illustrative flowchart of an inspection method according to an embodiment of the present disclosure. As shown in FIG. 2, in step S21, a CT scan is performed on the object being scanned to obtain projection data. For example, the CT scan is performed on the object being scanned by a single-energy or dual-energy CT scan device, so as to obtain multi-angle projection data.

In step S22, reconstruction is performed based on the projection data to obtain image data reflecting internal features of the object being scanned. For example, the reconstruction of the image may be performed by the computing unit 15 running a program, so as to obtain the 3D image of the object being scanned. In a case of dual-energy CT, the reconstruction is performed to obtain effective-atomic-number images and/or density images. In a case of single-energy CT, the reconstruction is performed to obtain attenuation-coefficient images or CT-number images.

In step S23, one or more organic and/or contraband parts of the object being scanned are determined. Then in step S24, display of the determined one or more organic and/or contraband parts are enhanced or highlighted relative to one or more other parts.

For example, the computing unit 15 distinguishes the organic part of the object being scanned from a non-organic part of the object being scanned, based on a physical attribute of the object being scanned, such as the attenuation coefficient, basis-material coefficient (which is obtained by decomposing basis-material in a dual-energy or multi-energy condition), CT number, density, effective atomic number, etc. In addition, the display unit 16 enhances contrast of the organic part of the object being scanned.

For example, most contraband in quarantine has one or more physical attributes different from those of other organics, such as the attenuation coefficient, basis-material coefficient, CT number, density, effective atomic number, etc. Identification of contraband in quarantine may be implemented by building a feature database of different substances for comparison in advance. Additionally, the CT system can also automatically identify primary contrabands in quarantine, such as fruits, vegetables, meat products, etc. by merging information about physical attributes, shape features, texture features, etc. And, the display unit 16 enhances the contrast of the contraband part of the object being scanned.

For example, the computing unit 15 may extend a display grayscale range of an organic and/or contraband part, and use all or a majority of the grayscale range for display of the organic and/or contraband part, improving display fineness of the organic and/or contraband part and contrast between organic and/or contraband parts; and may use a dedicated color scheme for assigning different types of organic substances with different colors, improving difference between visual effects of different organic substances including contrabands in quarantine. In addition, the computing unit 15 may also filter mixtures and metal substances out so as to avoid influencing an observation line of sight of the human operator, or may maintain the mixtures and the metal substances but enable them not to be rendered so obviously so as to avoid attracting attention of the human operator excessively. For another example, the system may automatically identify primary contrabands in quarantine, such as fruits, vegetables, meat products, etc., and emphasize them by adding one or more boxes, one or more arrows, by a flashing display, by special coloring, by a sound alarm, by a light alarm, etc.

In particular, compared to metal articles, organics, due to their weaker attenuation capability for X-rays, only occupy a upper small part of the grayscale range of the existing CT system, and thus are assigned with orange colors having different saturation degrees as usual, which causes non-obvious display of the organics in the 3D image of the object being scanned, and lower contrast between different types of organics. If there is no definite shape or texture information, the substance type of the organics cannot be particularly identified. Due to this, the CT system according to embodiments of the present disclosure may use all or a majority (e.g. no less than 80%) of the grayscale range for display of the organics including contrabands in quarantine, e.g., implementing a mapping of the physical attributes of organics and contrabands in quarantine to a larger grayscale range by a linear or segmentally linear way, or various non-linear ways, and may implement contrast enhancement of organics and contrabands in quarantine by performing global statistics or local statistics on the physical attributes or grayscales, so as to obtain the finest display effect which can present variations of surfaces or internal structures of the organics and/or contrabands.

In addition, the CT system according to embodiments of the present disclosure may use a dedicated color palette, which can contain violet, red, and/or yellow with different saturation degrees and various intermediate colors, besides orange with different saturation degrees, enabling organics and contrabands in quarantine with different physical properties to have different hues, thereby further improving the difference in visual effects of different organic substances including contrabands in quarantine. Since a human operator is not concern with the mixture and the metal, green and blue which are usually assigned to these two types of substances may also appear in the dedicated color palette. In addition, the 3D image may be pre-segmented, so that the same color is assigned to all of voxels in the same object, in order to improve uniform coloring of the object.

Figure 3:
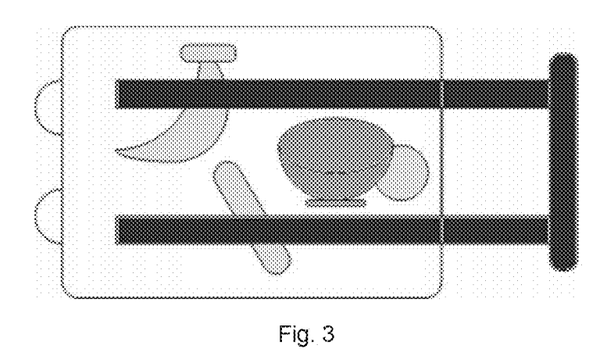
FIG. 3 shows a schematic view of an image of an object being scanned which is obtained by a conventional CT system.
Figure 4:
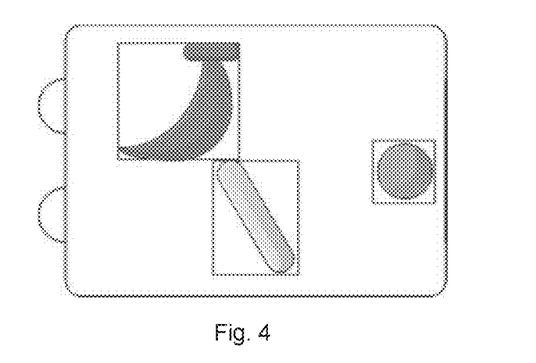
FIG. 4 shows a schematic view of an image which is obtained by a method according to an embodiment of the present disclosure.

In addition, the display unit 15 may hide the one or more non-organic and/or non-contraband parts, of the object being scanned. For example, the computing unit 15 may determine a foreground part of the image data; and remove pixels in the foreground part whose effective atomic number is larger than a predetermined value, so as to eliminate a shield of the foreground part of the organic part and/or contraband part. For the single-energy CT system, the image processing unit can restore the attenuation coefficient of an arbitrary position within the object, wherein the attenuation coefficient can partly reflect a material attribute of the object. For the dual-energy CT system, the computing unit 15 may also reconstruct the density and the effective atomic number of an arbitrary position within the object, wherein the effective atomic number can accurately reflect the material attribute of the object. The attenuation coefficient or the effective atomic number may be used for removing the mixture and the metal substances, e.g., rods of a suitcase, in the object being scanned, so as to avoid influencing the observation of the human operator. This is implemented by e.g. comparing the attenuation coefficient or the atomic number value with a predetermined threshold, in which pixels whose attenuation coefficient or atomic number value is higher than the threshold are weakened or not displayed. The attenuation coefficient or the effective atomic number may also be used for selecting the mixture and the metal substance in the object being scanned. By compressing the grayscale range, same color display, gray display or setting a higher transparency or a lower saturation degree, the mixture and the metal substance are not obvious in the 3D image, so that the human operator may focus on observing an organic and/or contraband. The metal rods of the suitcase in the conventional system as shown in FIG. 3 shield the organic and/or contraband part, which adversely affects the judgment of the human operator. However, as shown in FIG. 4, in the image obtained by the system according to embodiments of the present disclosure, the effect of the metal rods is eliminated, and the display of the contraband in quarantine is enhanced and highlighted, which facilitates the judgment of the human operator.

Most contraband in quarantine has physical attributes different from those of other organics, such as attenuation coefficient, density, effective atomic number, etc. By building a feature database of different substances for comparison in advance and improving the feature database continuously, the CT system can merge information about physical attributes, shape features, texture features, etc. to automatically identify primary contrabands in quarantine, such as fruits, vegetables, meat products, etc. For an identified contraband in quarantine, it can be emphasized by adding a box, an arrow, by a flashing display, by a special coloring (e.g. a bright red color) along with a sound and light alarm of the CT system, etc., so as to prompt the human operator to focus to have confirmation and manual inspection, which significantly improves the working effect and efficiency of quarantine supervision.

Figure 5:
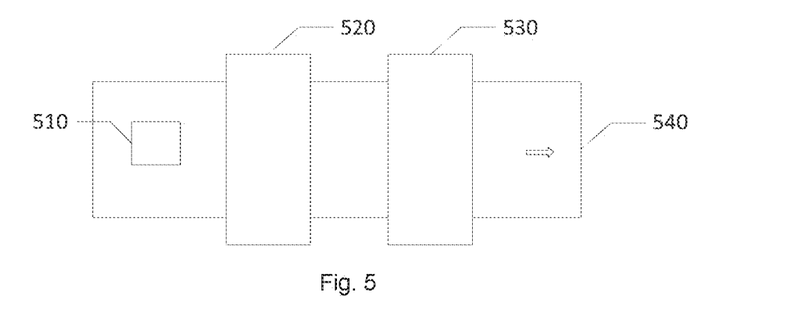
FIG. 5 shows a schematic view of an inspection system according to another embodiment of the present disclosure.

FIG. 5 shows a schematic view of an inspection system according to another embodiment of the present disclosure. In the embodiment as shown in FIG. 5, an object 510 being scanned is placed on a conveying apparatus 540 (e.g., a belt) for inspection, which sequentially passes through a DR system 520 and a dual-energy CT system 530. In the embodiment as shown in FIG. 5, the dual-energy CT system 530 and the DR system 520 may be operated synchronously.

Figure 6:
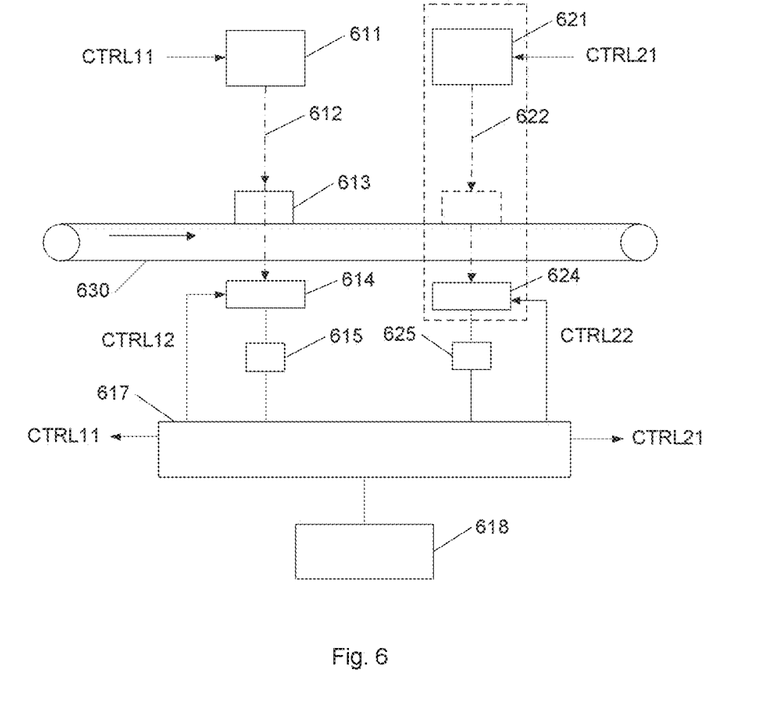
FIG. 6 shows a schematic structure diagram of the inspection system as shown in FIG. 5.

FIG. 6 shows a schematic structure diagram of the inspection system as shown in FIG. 5 in detail. The inspection device as shown in FIG. 6 includes a DR system on the left and a dual-energy CT system on the right, both of which share a conveying apparatus 630 bearing an object 613 being scanned to move ahead.

An X-ray source 611 for DR emits X-rays 612, which passes through the object 613 being scanned on the bearing mechanism 630; a transmission signal is received by a detector module 614; an analog signal is converted by a collection circuit 615 into a digital signal, which is transmitted to a controller 617 and a computer 618, etc. A transmission image of the object 613 being scanned is obtained in the computer 618, which is stored in a memory or is displayed.

In some embodiments, the ray source 611 may include a plurality of X-ray generators, e.g., distributed X-ray sources including a plurality of X-ray source points.

As shown in FIG. 6, the bearing mechanism 630 bears the object 613 being scanned to go through a scan area between the ray source 611 and the detector 614. In some embodiments, the detector 614 and the collection circuit 615 are e.g. detectors and data collectors in an integrated module structure, e.g., a plurality of detectors, for detecting the X-rays passing through an article being scanned so as to obtain the analog signal, and for converting the analog signal to the digital signal, thereby outputting projection data of the object being scanned for the X-rays. The controller 617 controls each part of the whole system to work synchronously. The computer 618 processes and reconstructs data collected by the data collector, and outputs the result.

According to the embodiment, the detector 614 and the collection circuit 615 are used for obtaining transmission data of the object 613 being scanned. A data amplifying circuit is included in the collection circuit 615, which may work in a (current) integrated manner or a pulse (counting) manner. The collection circuit 615 is connected to the controller 617 and the computer 618, and the collected data are stored in the computer 618 according to a trigger command.

In some embodiments, the detector module 614 includes a plurality of detection units for receiving the X-rays which pass through the object being scanned. The data collection circuit 615 is coupled to the detector module 614 for converting a signal generated by the detector module 614 to detection data. The controller 617 is connected via a control line CTRL11 to the X-ray source 611 and is connected via a control line CTRL12 to the detector module 514 which is in turn connected to the data collection circuit 615, so as to control at least one X-ray generator of the ray source to generate the X-rays which are emitted for passing through the object being scanned as the object moves. In addition, the controller 617 controls the detector module 614 and the data collection circuit 615 to obtain the detection data. The computing unit, such as a processor, in the computer 618 reconstructs the image of the object being scanned based on the detection data.

As the object being scanned keeps going ahead, the dual-energy CT system performs the CT scan on the object. An X-ray source 621 for CT emits X-rays 622, which pass through the object 613 being scanned on the bearing mechanism 630. As the object moves on, the X-ray source and a detector are rotated for the CT scan, a projection signal is received by the detector module 624, an analog signal is converted by a data collection circuit 625 into a digital signal, which is sent to the controller 617 and the computer 618, etc. Slice images of the object 613 being scanned are obtained in the computer 618, which are stored in the memory or are displayed.

In some embodiments, the detector module 624 includes a plurality of detection units for receiving the X-rays which pass through the object being scanned. The data collection circuit 625 is coupled to the detector module 624 for converting a signal generated by the detector module 624 to detection data. The controller 617 is connected via a control line CTRL21 to the X-ray source 621 and is connected via a control line CTRL22 to the detector module 624 which is in turn connected to the data collection circuit 625, so as to control two high and low energy X-ray generators of the X-ray source to alternately generate high and low energy X-rays which are emitted for passing through the object being scanned as the object being scanned moves, achieving the dual-energy CT scan. In addition, the controller 617 controls the detector module 624 and the data collection circuit 625 to obtain the projection data. The computing unit in the computer 618 reconstructs the image of the object being scanned based on the projection data, and performs substance identification.

As such, the DR system and the CT system operate synchronously. For example, before the CT scan, the DR scan is performed on the object being scanned to obtain the transmitted image; then the computer determines a position of a suspect contraband based on the transmission image; and the CT scan device performs the CT scan on at least a part of the object being scanned according to the position determined by the computing unit. In doing so, the CT scan may be performed on only the position of the possible suspect article, which improves the efficiency and accuracy of the inspection.

For example, in the embodiments as shown in FIGS. 5 and 6, the object being scanned goes through the DR system and the dual-energy CT system sequentially, and the obtained 2D and dual-energy 3D image data are input to the computer for substance identification. The substance identification system installed in the computer performs substance identification on the object being scanned according to the image data so as to obtain information of different substances, such as the effective atomic numbers, densities, etc., and tints the 2D image and the 3D image, automatically labeling the article which is judged as the object focused in quarantine (plant, animal, meat, etc.).

In an embodiment of the present disclosure, the substance identification system may hide a part of the object being scanned which is identified to be inorganic, so as to highlight one or more organic components of the object being scanned.

In an embodiment of the present disclosure, the substance identification system may further identify and distinguish the organics including contrabands in quarantine more accurately, respectively labeling plants, animals, meat, meat products, etc. with different colors. In addition, the image which has been labeled by substance identification is input to the image processing system in the computer 618, which in turn highlights the suspect object in quarantine and alarms automatically.

In addition, it may be understood by the skilled in the art that the DR scan does not need to be performed before the CT scan, and the CT scan is not necessarily performed according to the position of the suspect contraband determined from the DR image. For example, the DR system may be used as a supplement of the CT system to enable the human operator to continuously use the experiences of reading the 2D image.

In addition, the computer may automatically segment the image of the object being scanned which is mixed by multiple kinds of articles into separate articles according to their outline edges, facilitating a human operator to judge the image. Alternatively, the computer compares appearances of 3D images of the objects being scanned with templates in the suspect image database; and highlights suspect objects in connection with results of substance identification. Alternatively, the computer automatically identifies shape features of contrabands which are frequently labeled by a user and records the shape features in a database.

In an embodiment of the present disclosure, the image processing system in the computer 618 may be configured with a cloud data collection function, e.g., be connected to a cloud server for uploading the inspection data to the cloud server. The user may authorize different image inspection rights of the cloud server to different inspectors, or enable the image inspection rights of the cloud server to access to another management system.

Although the inspection devices for quarantine according to the present disclosure is described in connection with particular embodiments, the skilled in the art may apply the inspection devices to other fields for solving the inspection problem in other industries. Therefore, various modifications, improvements, expansions and applications which can be made by those skilled in the art based on the embodiments of the present disclosure are to be encompassed by the scope of the present disclosure as defined by the claims and their equivalents.

We claim:

1. An inspection system for quarantine, the system comprising:
a computed tomography (CT) scan device configured to perform a CT scan on an object being scanned to obtain projection data;
a computing unit configured to perform a reconstruction, based on the projection data, to obtain image data reflecting internal features of the object being scanned, and determine an organic and/or contraband part in the object being scanned; and
a display unit configured to enhance or highlight display of the determined organic and/or contraband part relative to another part, wherein the display and/or computer unit is configured to stretch a grayscale range for display of the organic and/or contraband part to a larger range.

2. The inspection system according to claim 1, wherein the organic and/or non-organic part of the object being scanned is distinguished based on a physical attribute of the object being scanned.

3. The inspection system according to claim 2, wherein the physical attribute comprises at least one selected from: attenuation coefficient, basis-material coefficient, CT number, density, and/or effective atomic number.

4. The inspection system according to claim 1, wherein the contraband part and a non-contraband part are distinguished based on at least one selected from: a physical attribute, a shape feature, and/or a texture feature, of the object being scanned.

5. The inspection system according to claim 4, wherein the contraband part and a non-contraband part are distinguished based on a physical attribute and the physical attribute comprises at least one selected from: attenuation coefficient, base-material coefficient, CT number, density, and/or effective atomic number.

6. The inspection system according to claim 1, wherein the CT scan device is configured to perform a single-energy CT scan or a dual-energy CT scan on the object being scanned; and the computing unit is configured to reconstruct an attenuation-coefficient image, a CT-value image or an effective-atomic-number image, of the object being scanned, and determine the organic and/or contraband part in the object being scanned according to at least one selected from: a shape feature, a texture feature, and/or a physical attribute.

7. The inspection system according to claim 1, wherein the display unit is configured to enhance contrast of the organic and/or contraband part of the object being scanned.

8. The inspection system according to claim 1, wherein the display unit is configured to indicate the organic and/or contraband part of the object being scanned.

9. The inspection system according to claim 8, wherein the display unit is configured to cause display of the organic and/or contraband part of the object being scanned with a box, an arrow, a flash or an assigned special color.

10. The inspection system according to claim 1, wherein the display unit is configured to hide a non-organic and/or non-contraband part of the object being scanned.

11. The inspection system according to claim 1, wherein the display unit is configured to weaken display of a non-organic and/or non-contraband part of the object being scanned.

12. The inspection system according to claim 11, wherein the display unit is configured to perform grayscale range reduction, same color display, gray display, transparency increase or saturation degree decrease on the non-organic part and/or non-contraband part of the object being scanned.

13. The inspection system according to claim 1, wherein the display unit is configured to weaken display of the non-organic and/or non-contraband part, while enhance display of the organic and/or contraband part.

14. The inspection system according to claim 1, wherein the computing unit is configured to determine a foreground part of the image data; and remove pixels in the foreground part whose attenuation coefficient, CT number and/or effective atomic number is larger than a predetermined value, so as to eliminate a shield by the foreground part of the organic and/or contraband part.

15. The inspection system according to claim 1, wherein the computing unit is configured to weaken pixels of the image data whose attenuation coefficient, CT number and/or effective atomic number is larger than a predetermined value.

16. The inspection system according to claim 1, wherein the computing unit is configured to identify contraband according to a template; and highlight an image of the contraband for the display unit.

17. The inspection system according to claim 1, further comprising a DR (Digital- Radiography) scan device configured to operate in synchronization with the CT scan device to obtain a transmitted image, and the inspection system is configured to cause display of a CT image and the transmitted image on a screen of the display unit.

18. The inspection system according to claim 1, wherein the computing unit is configured to automatically segment an image of the object being scanned, which is a mixture of multiple kinds of articles, into separate articles according to their outline edges, so as to facilitate a human operator to judge the image.

19. The inspection system according to claim 1, wherein the computing unit is configured to compare an appearance of a 3D image of the object being scanned with a template in a suspect image database; and highlight a suspect object in connection with a result of substance identification.

20. The inspection system according to claim 1, wherein the computing unit is configured to automatically identify shape features of contrabands which are frequently labeled by a user and record the shape features in a database.

21. The inspection system according to claim 7, wherein the computing unit is configured to divide organic parts and/or contraband parts into a plurality of sub-categories based on a classification standard, and assign different colors to pixels of object parts associated with different sub-categories.

22. An inspection method, comprising:
performing a computed tomography (CT) scan on an object being scanned to obtain projection data;
performing a reconstruction, based on the projection data, to obtain image data reflecting internal features of the object being scanned;
determining an organic and/or contraband part of the object being scanned; and
enhancing or highlighting display of the determined organic part and/or contraband part relative to another part,
wherein a grayscale range for display of the organic and/or contraband part is stretched to a larger range.

23. A non-transitory computer-readable medium comprising computer-executable instructions, when executed, configured to cause one or more processors to cause at least:
performance of a computed tomography (CT) scan on an object being scanned to obtain projection data;
performance of a reconstruction, based on the projection data, to obtain image data reflecting internal features of the object being scanned;
determination of an organic and/or contraband part of the object being scanned; and
enhancement or highlighting of display of the determined organic part and/or contraband part relative to another part,
wherein a grayscale range for display of the organic part and/or contraband part is stretched to a larger range.

24. The computer-readable medium of claim 23, wherein the instructions are further configured to cause the one or more processors to cause stretching of grayscale of pixels which are classified into organics or contrabands to a larger range.

* * * * *